US012564383B2

(12) United States Patent
Ma et al.

(10) Patent No.:  US 12,564,383 B2
(45) Date of Patent:       Mar. 3, 2026

(54) ENHANCED ULTRASOUND IMAGING APPARATUS AND ASSOCIATED METHODS OF WORK FLOW

(71) Applicant: FUJIFILM SonoSite, Inc., Bothell, WA (US)

(72) Inventors: Qinglin Ma, Woodinville, WA (US); Nikolaos Pagoulatos, Bothell, WA (US); Dave Glenn Willis, Woodinville, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 18/797,844

(22) Filed: Aug. 8, 2024

(65) Prior Publication Data

US 2024/0398384 A1      Dec. 5, 2024

Related U.S. Application Data

(62) Division of application No. 16/901,584, filed on Jun. 15, 2020, now Pat. No. 12,070,358, which is a division of application No. 15/356,504, filed on Nov. 18, 2016, now Pat. No. 10,792,016, which is a division of application No. 13/555,008, filed on Jul. 20, 2012, now Pat. No. 9,498,188.

(51) Int. Cl.
*A61B 8/00*              (2006.01)
(52) U.S. Cl.
CPC ............ *A61B 8/523* (2013.01); *A61B 8/4483* (2013.01); *A61B 8/463* (2013.01); *A61B 8/483* (2013.01)

(58) Field of Classification Search
None
See application file for complete search history.

(56) References Cited

U.S. PATENT DOCUMENTS

| | | | |
|---|---|---|---|
| 5,734,384 | A | 3/1998 | Yanof et al. |
| 5,891,030 | A | 4/1999 | Johnson et al. |
| | | (Continued) | |

OTHER PUBLICATIONS

Final Office Action received for U.S. Appl. No. 16/901,584, mailed on Dec. 29, 2023, 25 pages.

(Continued)

*Primary Examiner* — Katherine L Fernandez
(74) *Attorney, Agent, or Firm* — Womble Bond Dickinson (US) LLP

(57)                    ABSTRACT

Enhanced ultrasound imaging apparatus and associated methods of work flow are disclosed herein. In one embodiment, a method of ultrasound scanning includes receiving a first dataset representing ultrasonic scanning of a target anatomy of a patient in a two-dimensional mode and generating a two-dimensional ultrasound image of the scanned target anatomy based on the received first dataset. The method also includes accepting a definition of at least one of a sagittal plane, a transverse plane, and a coronal plane on the displayed two-dimensional ultrasound image. Thereafter, a second dataset representing ultrasonic scanning of the target anatomy in a three-dimensional mode is received and an ultrasound image at the coronal plane of the target anatomy is generated based on (1) the three-dimensional scanning and (2) the accepted definition of at least one of the sagittal plane, the transverse plane, and the coronal plane.

20 Claims, 8 Drawing Sheets

(56) References Cited

U.S. PATENT DOCUMENTS

| 6,775,404 | B1 | 8/2004 | Pagoulatos et al. |
| 7,130,457 | B2 | 10/2006 | Kaufman et al. |
| 9,498,188 | B2 | 11/2016 | Ma et al. |
| 2003/0013951 | A1 | 1/2003 | Stefanescu et al. |
| 2003/0016850 | A1* | 1/2003 | Kaufman ............... G16H 15/00 |
| | | | 382/128 |
| 2005/0090743 | A1 | 4/2005 | Kawashima et al. |
| 2005/0187474 | A1 | 8/2005 | Kwon |
| 2005/0245803 | A1 | 11/2005 | Glenn et al. |
| 2006/0033679 | A1 | 2/2006 | Gunji |
| 2009/0054776 | A1* | 2/2009 | Sasaki .................... A61B 8/483 |
| | | | 600/443 |
| 2010/0082365 | A1 | 4/2010 | Noordvyk et al. |
| 2011/0255762 | A1 | 10/2011 | Deischinger et al. |
| 2011/0282207 | A1* | 11/2011 | Hashimoto ........... A61B 8/466 |
| | | | 600/443 |

OTHER PUBLICATIONS

Notice of Allowance received for U.S. Appl. No. 16/901,584, mailed on May 8, 2024, 10 pages.

* cited by examiner

Fallopian Tube

Fundus
(top of uterine cavity)

Ovary

Endometrium

Myometrium

Cervix

Vagina

Adenomyosis
106

Bicornate Uterus

108
Ovarian Cyst

102
Fibroids Submucosal

102
Fibroids Intramural

104
Polyp

102
Fibroids
Subserosal

110
Partial Septum

Normal     Subseptate     Bicornuate Unicolis

Septus     Bicornuate     Didelphys     Uncolis

302

304

302

212

214

ENHANCED ULTRASOUND IMAGING APPARATUS AND ASSOCIATED METHODS OF WORK FLOW

CROSS-REFERENCES TO RELATED APPLICATIONS

This application is a divisional application of U.S. patent application Ser. No. 16/901,584, filed on Jun. 15, 2020, entitled "ENHANCED ULTRASOUND IMAGING APPARATUS AND ASSOCIATED METHODS OF WORK FLOW" which is a divisional application of U.S. patent application Ser. No. 15/356,504, filed on Nov. 18, 2016, entitled "ENHANCED ULTRASOUND IMAGING APPARATUS AND ASSOCIATED METHODS OF WORK FLOW," now U.S. Pat. No. 10,792,016 issued on Oct. 6, 2020, which is a divisional application of U.S. patent application Ser. No. 13/555,008, filed on Jul. 20, 2012, and entitled "ENHANCED ULTRASOUND IMAGING APPARATUS AND ASSOCIATED METHODS OF WORK FLOW," now U.S. Pat. No. 9,498,188 issued on Nov. 22, 2016, which are hereby incorporated herein in their entireties by reference.

TECHNICAL FIELD

The present application is generally related to 3-D/4-D ultrasound imaging apparatus and associated methods of work flow.

BACKGROUND

Ultrasound volume imaging is capable of recording and/or displaying three- or four-dimensional visual information of a human anatomy. Such techniques have been used for visualizing and/or diagnosing conditions relating to obstetrics, gynecology, and cardiology. For example, ultrasound volume imaging can be used in gynecology to visualize and/or diagnose various uterus abnormalities. FIG. 1A shows a cross-sectional view of normal female reproductive organs. In contrast, FIG. 1B shows a cross-sectional view of female reproductive organs with various abnormalities including fibroids, a polyp, adenomyosis, an ovarian cyst, and a partial septum. In another example, ultrasound volume imaging can also be used to assess uterine shapes for infertility diagnosis. It is believed that uteri may have some variations that correlate to high risks of miscarriage, uterus eruption, and/or other adverse conditions affecting pregnancy. Several examples of common uterus variations are shown in FIG. 2.

Diagnosing some of the foregoing conditions can include visualizing a three-dimensional image of the human anatomy along different planes. For example, as shown in FIG. 3, the human anatomy may be visualized relative to the sagittal, coronal, and transverse planes of a human body. A conventional technique for visualizing the human anatomy along such planes includes manipulating the three-dimensional image of the human anatomy using rotating, panning, scaling, and/or other suitable planar editing tools that require input from the technician or doctor. As discussed in more detail later, this technique can be time-consuming and inefficient because it requires a significant amount of three-dimensional thinking and anatomical familiarity. Accordingly, several improvements may be needed to efficiently produce the desired visualization of three-dimensional images along these planes.

DETAILED DESCRIPTION

The present technology is directed to enhanced ultrasound imaging apparatus and associated methods of work flow. As used herein, the term "three-dimensional" (or "3-D") images generally refers to images having three dimensions that do not lie in the same plane. The term "four-dimensional" (or "4-D") image generally refers to a sequence of 3-D images over time. It will be appreciated that several of the details set forth below are provided to describe the following embodiments in a manner sufficient to enable a person skilled in the relevant art to make and use the disclosed embodiments. Several of the details described below, however, may not be necessary to practice certain embodiments of the technology. Additionally, the technology can include other embodiments that are within the scope of the claims but are not described in detail with respect to FIGS. 4A-9.

Figures 4A, 4B:
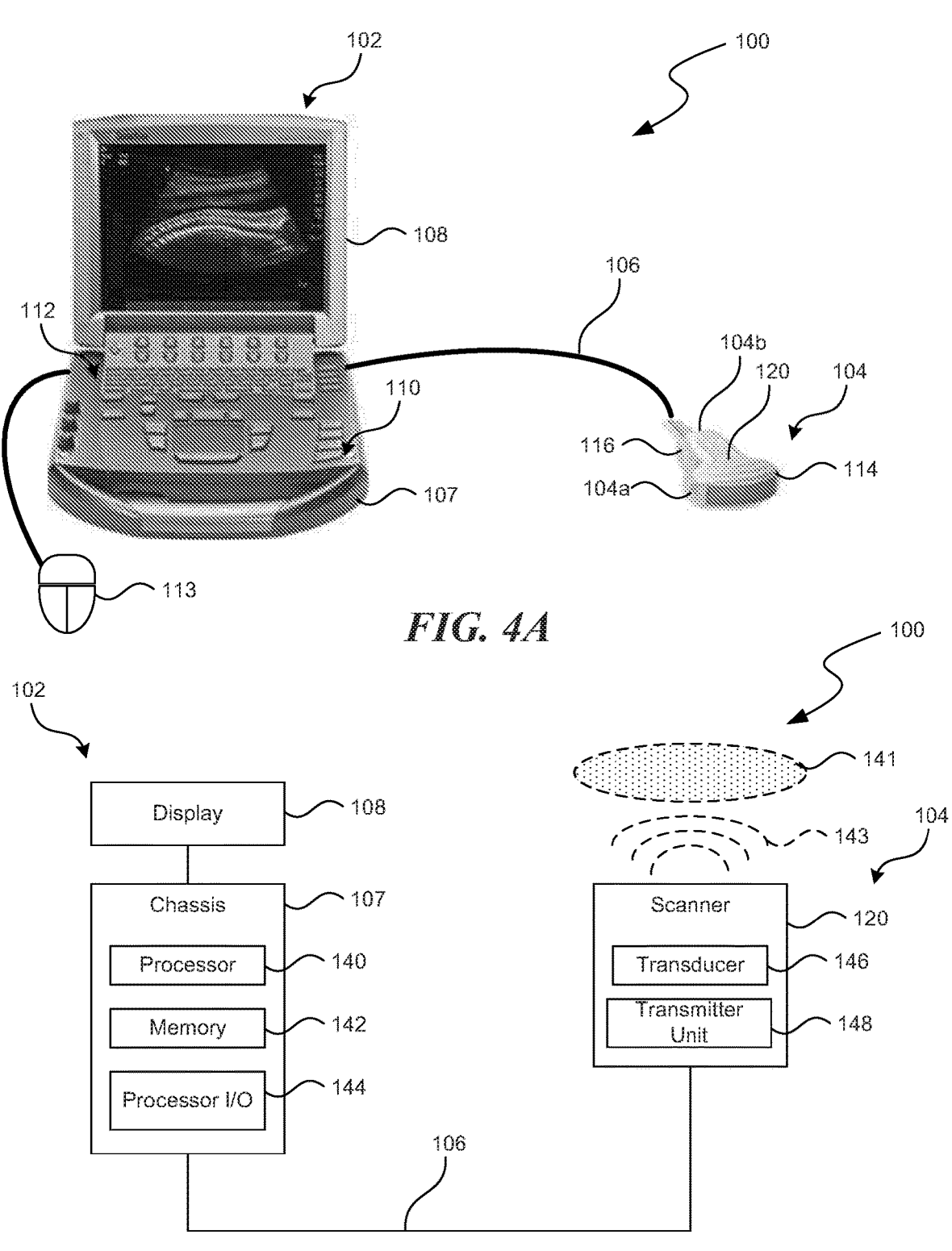
FIG. 4A is a perspective view of an ultrasound imaging apparatus in accordance with an embodiment of the technology.
FIG. 4B is a schematic logic diagram of the ultrasound imaging apparatus in FIG. 4A.

FIG. 4A is a perspective view and FIG. 4B is a schematic logic diagram of an ultrasound imaging apparatus 100 in accordance with embodiments of the technology. As shown in FIG. 4A, the ultrasound imaging apparatus 100 can include a processing station 102 coupled to an ultrasound scanner 104 with a communication link 106. In one embodiment, the communication link 106 includes a plurality of coaxial or other type of hardwire cables. In other embodiments, the communication link 106 can include a wireless link, an internet link, an intranet link, and/or another suitable communication connection.

As shown in FIG. 4A, the processing station 102 is a mobile device that includes a chassis 107 operatively coupled to a display 108. The chassis 107 can carry one or more buttons 110, a keyboard 112, a mouse 113, a stylus (not shown), and/or other suitable input/output components. The display 108 can include a liquid crystal display, a plasma display, a touchscreen, and/or another suitable graphic display. In other embodiments, the processing station 102 can be a handheld device, a cart-mounted device, a fixed-mounted device, or another suitable type of device.

The ultrasound scanner 104 can include a housing 120 with a scan head 114 at a distal end 104a and a hand grip 116 at a proximal end 104b. In the illustrated embodiment, the scan head 114 and the hand grip 116 of the ultrasound scanner 104 form generally a "T" shape. In other embodiments, the scan head 114 and the hand grip 116 can have other suitable geometric configurations based on particular applications. As described in more detail below with reference to FIG. 4B, the ultrasound scanner 104 can further include an ultrasound transducer array in the scan head 114 at the distal end 104a, electronic data processing components in the housing 120, and/or other suitable mechanical or electrical components (not shown in FIG. 4A) in the housing 120.

As shown in FIG. 4B, the processing station 102 can include a logic processor 140, a memory 142 operatively coupled to the logic processor 140, and a processor input/output component 144. The logic processor 140 can include a microprocessor, a field-programmable gate array, and/or other suitable logic devices. The memory 142 can include volatile and/or nonvolatile computer storage media (e.g., ROM, RAM, magnetic disk storage media, optical storage media, flash memory devices, and/or other suitable computer readable media) configured to store data received from, as well as instructions for, the logic processor 140. The processor input/output component 144 can include device drivers configured to accept input from and provide output to an operator via the keyboard 112 (FIG. 4A), the buttons 110 (FIG. 4A), the display 108, and/or other suitable interfacing components of the processing station 102.

In the embodiment shown in FIG. 4B, the ultrasound scanner 104 includes an ultrasound transducer 146 operatively coupled to the processor input/output component 144 via the communication link 106. In one embodiment, the ultrasound transducer 146 includes a single transducer element. In other embodiments, the ultrasound transducer array 146 can include an array of individual piezoelectric transducer elements (e.g., 256 lead zirconate titanate elements) and/or other suitable transducer elements.

Referring to both FIGS. 4A and 4B, in operation, an operator (not shown) holds the ultrasound scanner 104 by the hand grip 116 and places the distal end 104a of the ultrasound scanner 104 proximate to or in contact with a structure to be examined, for example, a target anatomy 141 of a patient (shown in phantom lines for clarity). The ultrasound transducer array 146 then transmits sound waves 143 into the target anatomy 141 and detects echoes returning from the target anatomy 141. The ultrasound transducer array 146 can then convert the detected echoes into electrical signals representing the detected echoes.

Figure 5:
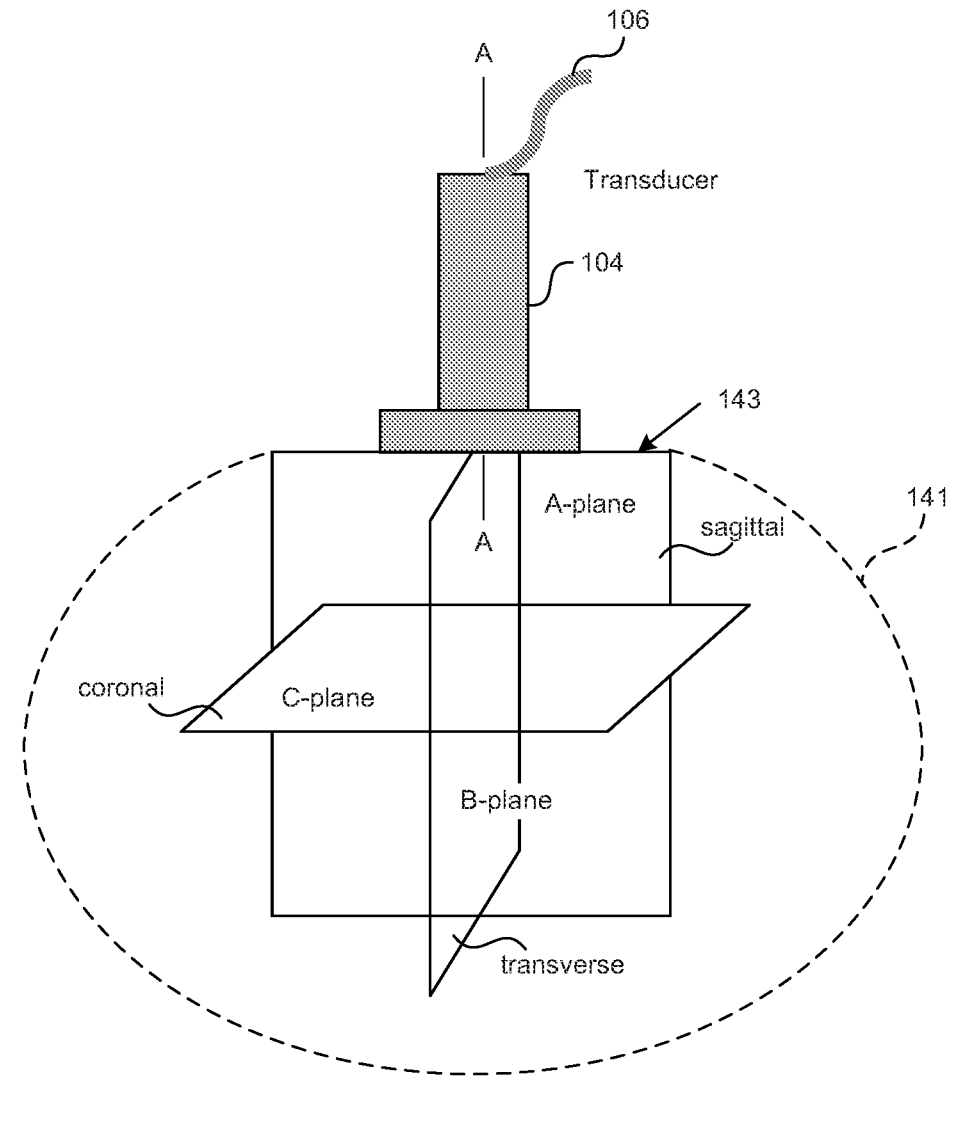
FIG. 5 is a perspective view of a target anatomy showing naming conventions for 3-D cut planes in accordance with an embodiment of the technology.

The processing station 102 receives the electrical signals from the ultrasound scanner 104 via the communication link 106 and the processor input/output component 144. The processing station 102 can process the received electrical signals to generate, record, and/or display a two-dimensional (or "2-D") image along certain planes of the target anatomy 141 based on the received data. FIG. 5 is a perspective view of the target anatomy 141 showing naming conventions for 3-D cut planes or multi-planar-rendered ("MPR") planes.

Figures 1A, 1B:
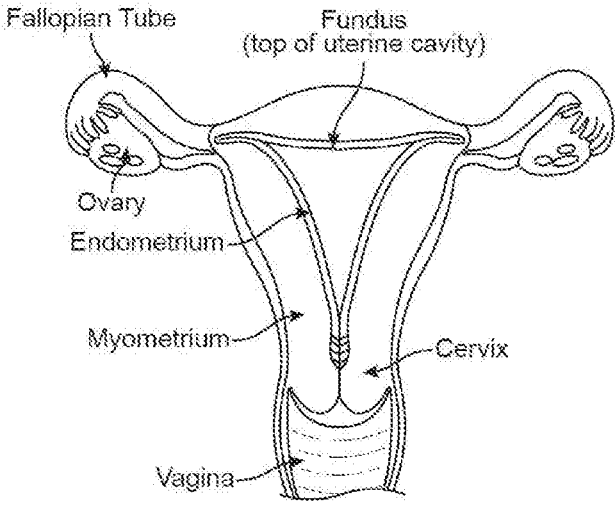
FIG. 1A is a cross-sectional view of normal female reproductive organs.
FIG. 1B is a cross-sectional view of female reproductive organs with certain abnormalities.
Figure 2:
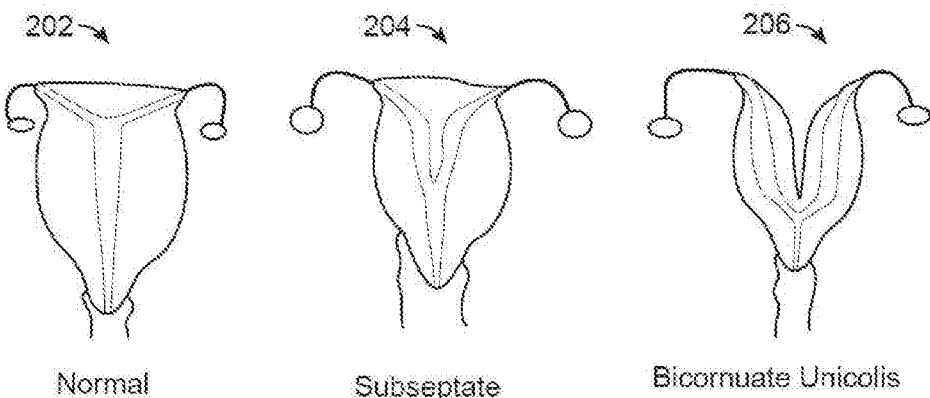
FIG. 2 illustrates certain variations in uterus shapes.
Figure 2:
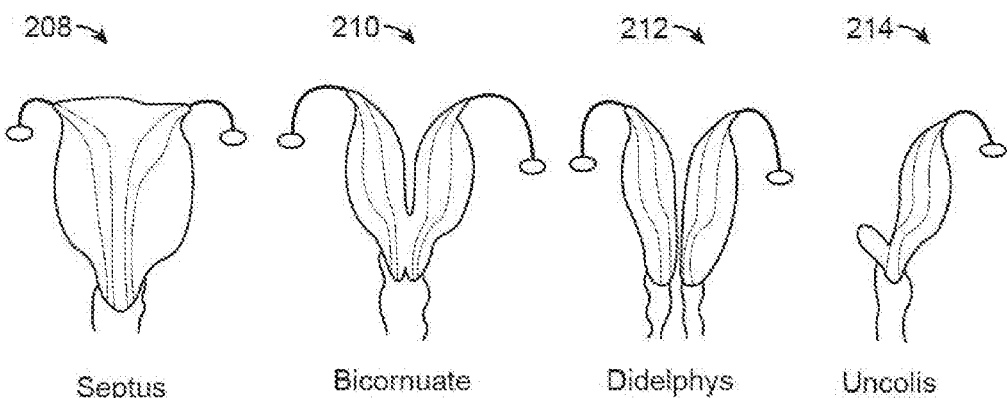
Figure 3:
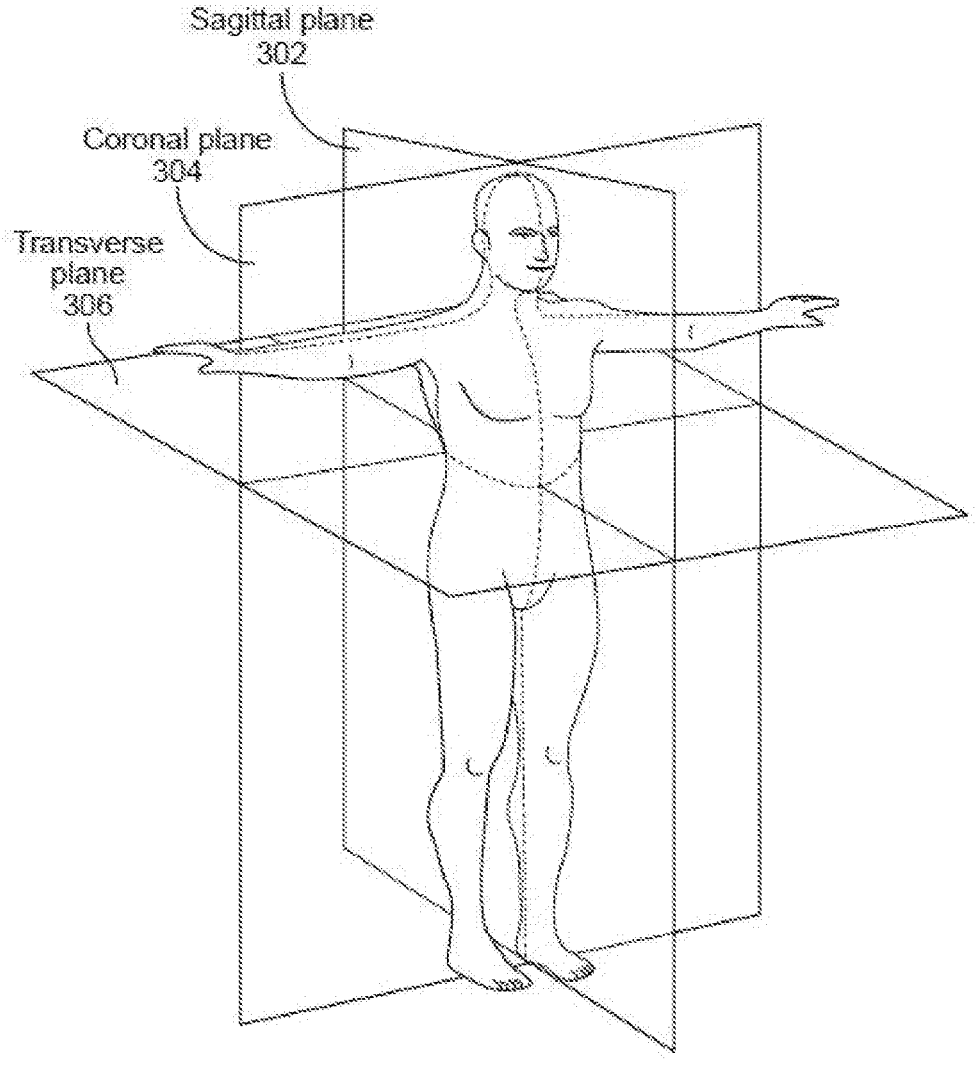
FIG. 3 is a perspective view of a human body illustrating the sagittal, coronal, and transverse planes.

As shown in FIG. 5, the target anatomy 141 may be divided along three generally orthogonal cut planes, i.e., an A-plane, a B-plane, and a C-plane. The A-, B-, and C-planes typically correspond to the sagittal, transverse, and coronal planes (FIG. 3) relative to a human body, respectively. The processing station 102 can produce 2-D images of the target anatomy along the A-plane (i.e., the sagittal plane) and the B-plane (i.e., the transverse plane) when the operator rotates the ultrasound scanner 104 about axis A-A between A- and B-planes. However, as shown in FIG. 5, the C-plane images (i.e., the coronal plane) typically cannot be obtained by rotating the ultrasound scanner 104 because the target anatomy 141 typically blocks such a movement. In certain applications, the C-plane images are more important than the A-plane and B-plane images for diagnosing polyp, bicornuate uterus, and/or other uterus abnormalities, as shown by FIG. 2.

The C-plane images though, may be obtained through 3-D/4-D volume imaging. A conventional technique for producing C-plane images from a 3-D/4-D image involves turning and rotating the 3-D/4-D image after starting 3-D/4-D volume imaging. Such a technique, however, requires a significant amount of three-dimensional thinking and anatomical familiarity by the operator because the 3-D/4-D images typically do not include any anatomic landmarks. Several embodiments of the ultrasound imaging apparatus 100 can address the foregoing drawbacks by allowing the operator to define at least one MPR plane in a 2-D image of the target anatomy 141 using anatomic landmarks prior to starting 3-D/4-D volume imaging and automatically producing the C-plane images without further manipulation of the 3-D/4-D volume image dataset, as discussed in more detail below with reference to FIGS. 6-9.

Figure 6:
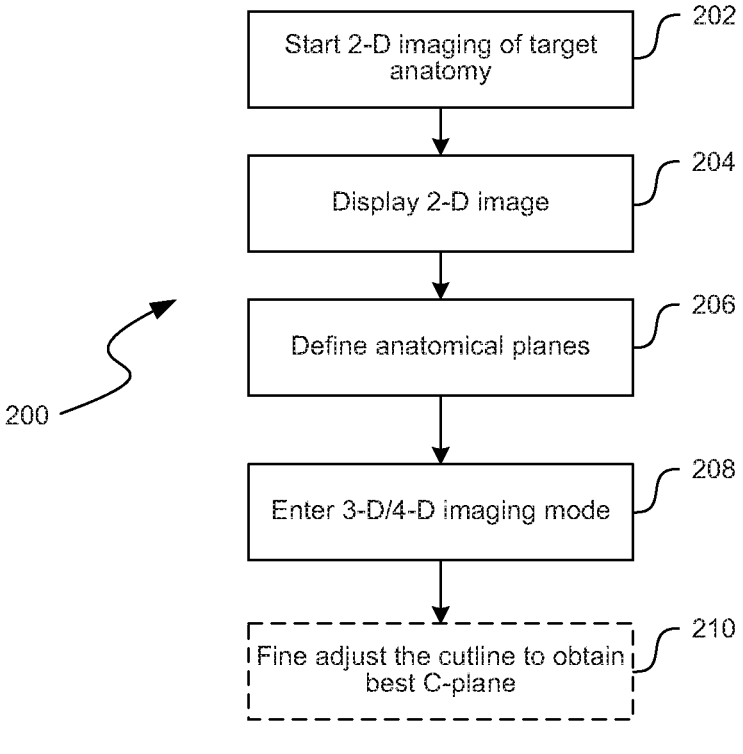
FIG. 6 is a flowchart showing a method of work flow for generating 3-D/4-D images of a target anatomy in accordance with an embodiment of the present technology.

FIG. 6 is a flowchart showing a method of work flow 200 for generating cut-plane images of 3-D/4-D imaging of a target anatomy in accordance with embodiments of the present technology. In the following discussion, a uterus is used as an example of a target anatomy although several embodiments of the technique may also be applied to a heart, a fetus, and/or other suitable target anatomies.

As shown in FIG. 6, an initial stage of the method 200 (block 202) includes starting 2-D imaging of the uterus. In one embodiment, the processing station 102 (FIG. 4A) can send a command to the ultrasound scanner 104 (FIG. 4A) to simultaneously scan a plane (e.g., A- or B-plane) at least proximate the target anatomy. Such scanning is typically referred to as scanning in B-mode. The processing station 102 can then receive a first dataset that represents a 2-D image of the uterus from the ultrasound scanner 104. In another embodiment, the ultrasound scanner 104 may scan the target anatomy using line scanning (typically referred to as A-mode), and the processing station 102 may assemble the first dataset based on the data corresponding to the A-mode scanning. In other embodiments, the processing station 102 may receive a dataset that represents a 3-D/4-D volume scanning of the target anatomy from the ultrasound scanner 104. The processing station 102 may then analyze the received dataset (e.g., using A-plane images) to generate the first dataset corresponding to at least one 2-D image of the uterus.

Another stage of the method 200 (block 204) can include rendering the generated 2-D image of the uterus on the display 108 (FIG. 4A). In one embodiment, the 2-D image may be generated and/or displayed when the processing station 102 is in 2-D scanning mode. In another embodiment, the 2-D image may be displayed when the processing station 102 is in "setup" mode before initiating 3-D/4-D scanning. In further embodiments, the 2-D image may be displayed in other suitable operating modes.

A subsequent stage of the method 200 (block 206) includes defining anatomical planes of the uterus based on the displayed 2-D image. In one embodiment, the anatomical planes can include at least one of the A-, B-, and C-planes defined by placing cut lines on the displayed 2-D image. The operator can then provide an input indicating correspondence between the cut lines and at least one of the A-, B-, and C-planes. In another embodiment, the anatomical planes may be defined using other suitable techniques.

Based on the defined anatomical planes, another stage (block 208) of the method 200 includes initiating 3-D/4-D volume imaging and automatically producing the A-, B-, and C-plane images. During 3-D/4-D volume imaging, the ultrasound scanner 104 may provide a second dataset to the processing station 102 representing a volume image of the uterus. In one embodiment, the processing station 102 may use the relative placement of the cut line(s) as a criterion and generate an ultrasound image that is orthogonal to the placed cut line. For example, the two-dimensional ultrasound image may be at the sagittal plane or the transverse plane. The processing station 102 may receive data (e.g., starting and/or ending coordinates of lines, shapes, etc.) representing a placement of a first cut line and a second cut line relative to the two-dimensional ultrasound image. The processing station 102 may then receive an input indicating that the first cut line corresponds to one of the sagittal plane and the transverse plane, and that the second cut line corresponds to the coronal plane.

Based on the input, the processing station 102 may then process the second dataset to generate ultrasound images at additional and/or different planes. For example, in one embodiment, the processing station 102 generates an ultrasound image at the C-plane. In another embodiment, images along at least two of the sagittal, transverse, and coronal planes may be generated. An optional stage (block 210) of the method 200 includes fine-adjusting the 3-D/4-D imaging to obtain a desired C-plane image.

Figure 7A:
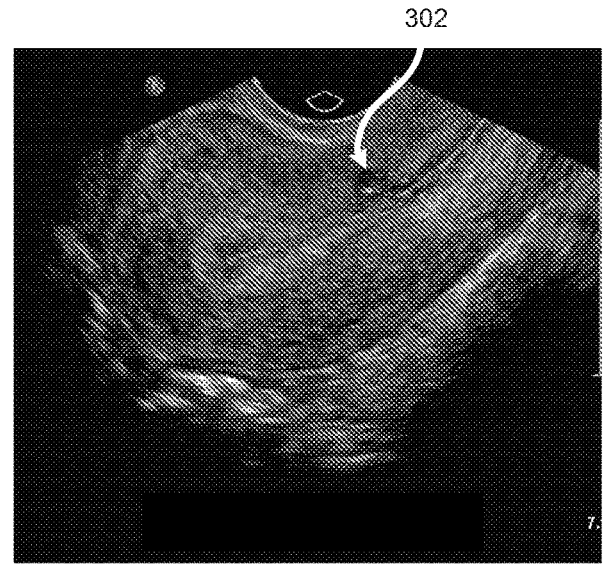
FIGS. 7A-7C are 2-D ultrasonic images of a target anatomy during certain stages of the method of work flow in FIG. 6.
Figure 7B:
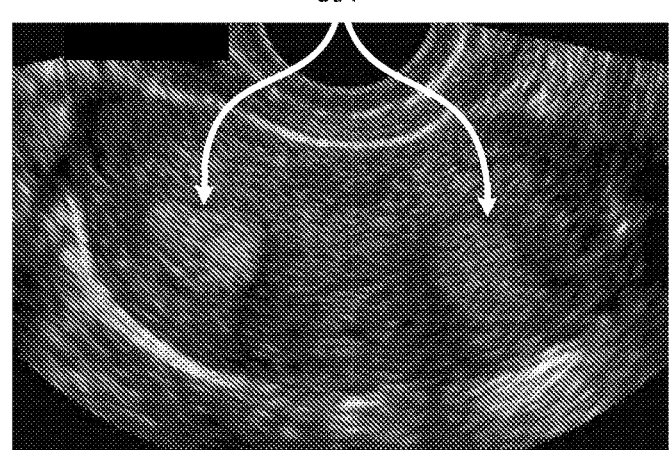
Figure 7C:
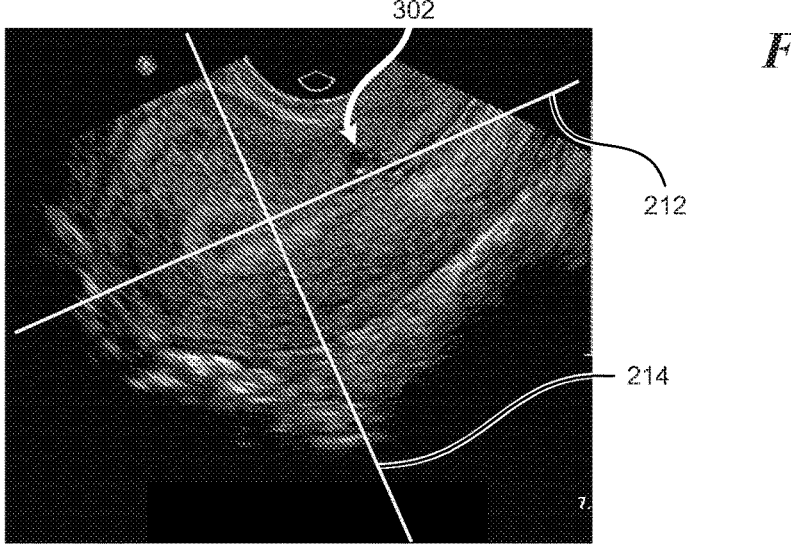

FIGS. 7A-9 illustrate ultrasonic images of the uterus during several stages of the method 200 in FIG. 6. FIGS. 7A and 7B are 2-D A-plane and B-plane views, respectively, of the uterus. In FIG. 7A, the illustrated image shows a scar 302 from a previous Caesarian section. In FIG. 7B, the illustrated image shows a bicornuate uterus 304. An operator can then define anatomical planes of the target anatomy based on the displayed 2-D image. For example, as shown in FIG. 7C, the operator may define the B-plane and the C-plane by placing the first and second cut lines 212 and 214 on the displayed 2-D image, respectively. The first and second cut lines 212 and 214 may be placed by defining a starting point and an end point of the first and second cut lines 212 and 214, by drawing a line with the mouse 113 (FIG. 4A), and/or via other suitable means.

Figure 8:
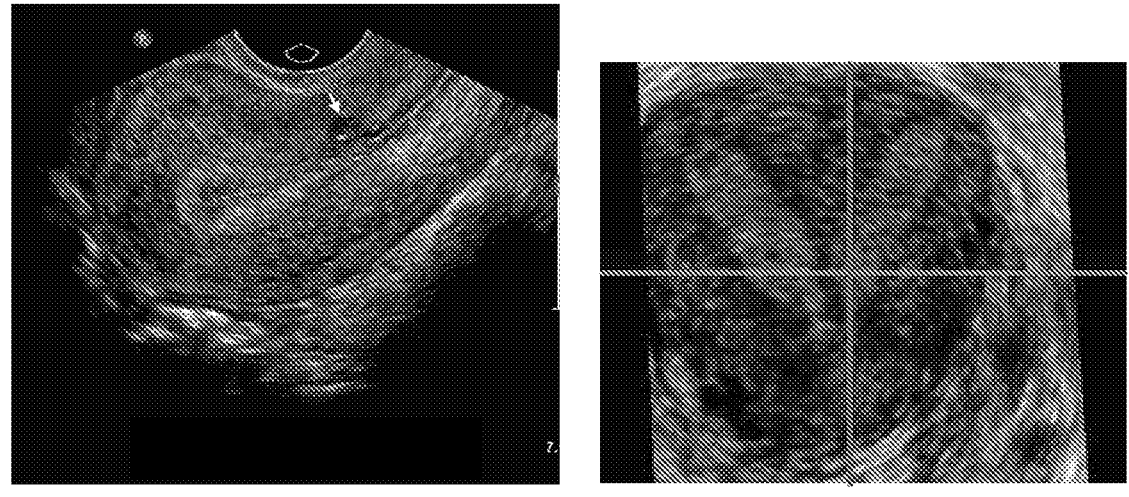
FIGS. 8 and 9 are ultrasonic images of a target anatomy during other stages of the method of work flow in FIG. 6.
Figure 9:
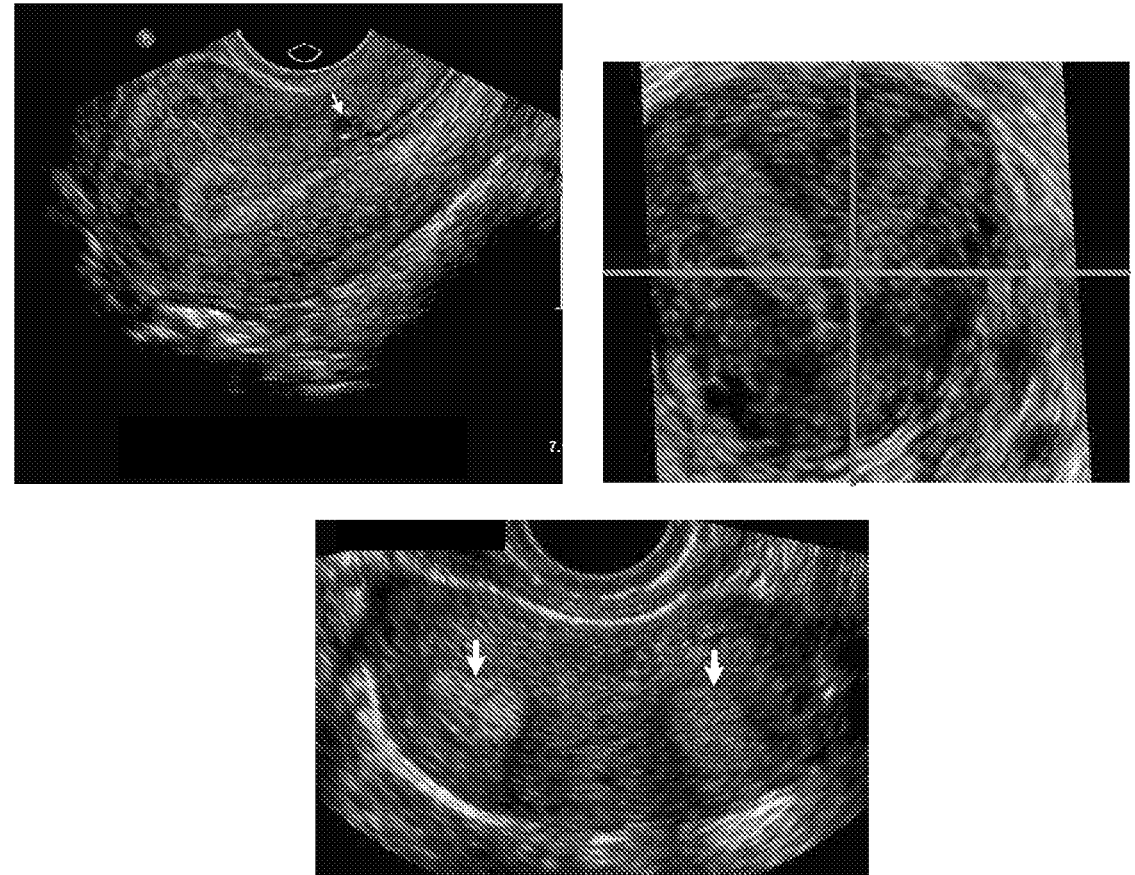

Subsequently, 3-D/4-D volume imaging may be started. Based on the cut lines defined in FIG. 7C, images at different anatomical planes may be automatically generated. For example, FIG. 8 shows the images at the A-plane and the C-plane in a side-by-side arrangement. In another example, as shown in FIG. 9, the images at the A-plane (upper left), the B-plane (lower), and the C-plane (upper right) may be shown together. In further examples, at least some of these images may be shown with the 3-D/4-D images, and/or may have other suitable display configurations.

From the foregoing, it will be appreciated that specific embodiments of the technology have been described herein for purposes of illustration, but that various modifications may be made without deviating from the disclosure. Many of the elements of one embodiment may be combined with other embodiments in addition to or in lieu of the elements of the other embodiments. Accordingly, the disclosure is not limited except as by the appended claims.

What is claimed is:

1. A method of ultrasound scanning, comprising:
placing an ultrasound scanner relative to a target anatomy of a patient along a first anatomical plane that is one of a sagittal plane and a transverse plane;

using the ultrasound scanner to scan the target anatomy along the first anatomical plane to produce a two-dimensional ultrasound image of the scanned target anatomy representing the first anatomical plane;
receiving a first input indicating placement of a first cut line on the two-dimensional ultrasound image;
receiving a second input indicating a correspondence between the first cut line and a second anatomical plane, the second anatomical plane including at least one of the sagittal plane, the transverse plane, and a coronal plane and being different than the first anatomical plane;
defining the second anatomical plane based on the first cut line and the correspondence; and
thereafter, using the ultrasound scanner to initiate volume scanning of the target anatomy, generating an additional ultrasound image at the second anatomical plane of the target anatomy based on the defined second anatomical plane.

2. The method of claim 1, further comprising defining a third anatomical plane on the produced two-dimensional ultrasound image, the third anatomical plane being orthogonal to the second anatomical plane.

3. The method of claim 1, wherein the first cut line on the produced two-dimensional ultrasound image is placed based on an anatomical landmark in the produced two-dimensional ultrasound image.

4. The method of claim 3, further comprising:
displaying the first cut line on the two-dimensional image.

5. The method of claim 1, wherein the additional ultrasound image is orthogonal to the two-dimensional ultrasound image.

6. The method of claim 1, wherein defining the second anatomical plane includes defining the coronal plane on the produced two-dimensional ultrasound image.

7. The method of claim 1, wherein the first anatomical plane comprises the sagittal plane; wherein defining the second anatomical plane includes defining the coronal plane on the produced two-dimensional ultrasound image; and the method further includes defining a third anatomical plane on the produced two-dimensional ultrasound image, the third anatomical plane being the transverse plane.

8. An ultrasound system, comprising:
an ultrasound scanner;
a communication link attached to the ultrasound scanner; and
a processing station operatively coupled to the ultrasound scanner via the communication link, the processing station having
a display,
a memory, and
a processor coupled to the memory and the display, wherein the ultrasound scanner is configured to be positioned relative to a target anatomy of a patient along a first anatomical plane that is one of a sagittal plane and a transverse plane to scan the target anatomy along the first anatomical plane to produce a two-dimensional ultrasound image of the scanned target anatomy representing the first anatomical plane on the display, and wherein the processor is configured to:
receive a first input indicating placement of a first cut line on the two-dimensional ultrasound image;
receive a second input indicating a correspondence between the first cut line and a second anatomical plane, the second anatomical plane including at least one of the sagittal plane, the transverse plane, and a coronal plane and being different than the first anatomical plane;

define the second anatomical plane based on the first cut line and the correspondence; and thereafter, using the ultrasound scanner, initiate volume scanning of the target anatomy to generate an additional ultrasound image at the second anatomical plane of the target anatomy based on the defined second anatomical plane.

9. The ultrasound system of claim 8, wherein the processor is configured to define a third anatomical plane on the produced two-dimensional ultrasound image, the third anatomical plane being orthogonal to the second anatomical plane.

10. The ultrasound system of claim 8, wherein the first cut line on the produced two-dimensional ultrasound image is based on an anatomical landmark in the produced two-dimensional ultrasound image.

11. The ultrasound system of claim 10, wherein the processor is further configured to:

display the first cut line on the two-dimensional image.

12. The ultrasound system of claim 10, wherein defining the second anatomical plane includes defining the coronal plane on the produced two-dimensional ultrasound image.

13. The ultrasound system of claim 8, wherein the first anatomical plane comprises the sagittal plane; wherein the second anatomical plane includes the coronal plane; and the wherein the processor is further configured to: receive a third input indicating placement of a second cut line on the two-dimensional ultrasound image; receive a fourth input indicating the correspondence between the second cut line and a third anatomical plane on the produced two-dimensional ultrasound image, the third anatomical plane being the transverse plane.

14. The ultrasound system of claim 8, wherein the additional ultrasound image is orthogonal to the two-dimensional ultrasound image.

15. A non-transitory computer-readable medium containing instructions that, when executed, cause an ultrasound system comprising an ultrasound scanner and a processor coupled to the ultrasound scanner to perform operations comprising:

scanning, using the ultrasound scanner, a target anatomy of a patient along a first anatomical plane to produce a two-dimensional ultrasound image of the scanned target anatomy representing the first anatomical plane, wherein the ultrasound scanner is placed relative to the target anatomy along the first anatomical plane that is one of a sagittal plane and a transverse plane;

receiving, using the processor, a first input indicating placement of a first cut line on the two-dimensional ultrasound image;

receiving, using the processor, a second input indicating a correspondence between the first cut line and a second anatomical plane, the second anatomical plane including at least one of the sagittal plane, the transverse plane, and a coronal plane and being different than the first anatomical plane;

defining, using the processor, the second anatomical plane based on the first cut line and the correspondence; and thereafter, using the ultrasound scanner to initiate volume scanning of the target anatomy, generating an additional ultrasound image at the second anatomical plane of the target anatomy based on the defined second anatomical plane.

16. The non-transitory computer-readable medium of claim 15, wherein the operations further comprise: defining a third anatomical plane on the produced two-dimensional ultrasound image, the third anatomical plane being orthogonal to the second anatomical plane.

17. The non-transitory computer-readable medium of claim 15, wherein the first cut line on the produced two-dimensional ultrasound image is placed based on an anatomical landmark in the produced two-dimensional ultrasound image.

18. The non-transitory computer-readable medium of claim 15, wherein defining the second anatomical plane includes defining the coronal plane on the produced two-dimensional ultrasound image.

19. The non-transitory computer-readable medium of claim 15, wherein the first anatomical plane comprises the sagittal plane; wherein the second anatomical plane includes the coronal plane; and the operations further comprise: receiving a third input indicating placement of a second cut line on the two-dimensional ultrasound image; receive a fourth input indicating the correspondence between the second cut line and a third anatomical plane on the produced two-dimensional ultrasound image, the third anatomical plane being the transverse plane.

20. The non-transitory computer-readable medium of claim 15, wherein the additional ultrasound image is orthogonal to the two-dimensional ultrasound image.

* * * * *